(12) United States Patent
Holmqvist

(10) Patent No.: US 9,233,212 B2
(45) Date of Patent: Jan. 12, 2016

(54) DEVICE FOR REMOVING DELIVERY MEMBER SHIELDS

(71) Applicant: SHL GROUP AB, Nacka Strand (SE)

(72) Inventor: Anders Holmqvist, Värmdö (SE)

(73) Assignee: SHL GROUP AB, Nacka Strand (SE)

( * ) Notice: Subject to any disclaimer, the term of this patent is extended or adjusted under 35 U.S.C. 154(b) by 0 days.

(21) Appl. No.: 14/351,918

(22) PCT Filed: Oct. 2, 2012

(86) PCT No.: PCT/SE2012/051051
§ 371 (c)(1),
(2) Date: Apr. 15, 2014

(87) PCT Pub. No.: WO2013/058697
PCT Pub. Date: Apr. 25, 2013

(65) Prior Publication Data
US 2014/0343503 A1    Nov. 20, 2014

Related U.S. Application Data

(60) Provisional application No. 61/547,913, filed on Oct. 17, 2011.

(30) Foreign Application Priority Data

Oct. 17, 2011    (SE) ........................ 1150962

(51) Int. Cl.
*A61M 5/32*    (2006.01)
*A61M 5/20*    (2006.01)

(52) U.S. Cl.
CPC ............... *A61M 5/3204* (2013.01); *A61M 5/20* (2013.01); *A61M 5/3202* (2013.01)

(58) Field of Classification Search
CPC ............ A61M 5/3202; A61M 5/3204; A61M 5/3213; A61M 5/3205; A61M 2005/3139; A61M 5/20; A61M 2005/3215; A61M 2205/586
USPC .......................... 604/192–198, 110, 207–212
See application file for complete search history.

(56) References Cited

U.S. PATENT DOCUMENTS 5,098,400 A * 3/1992 Crouse et al. ................. 604/192
7,094,223 B2 * 8/2006 Brunel .......................... 604/192
(Continued)

FOREIGN PATENT DOCUMENTS

GB          2465389         5/2010
WO          03/051423       6/2003
(Continued)

OTHER PUBLICATIONS

International Search Report and Written Opinion for Int. App. No. PCT/SE2012/051051, mailed Jan. 29, 2013.

*Primary Examiner* — Bhisma Mehta
*Assistant Examiner* — Hamza Darb
(74) *Attorney, Agent, or Firm* — McDonnell Boehnen Hulbert & Berghoff LLP

(57) ABSTRACT

The present invention relates to a device for removing delivery member shields which are intended to cover and protect delivery members, said device comprising a remover body arranged to accommodate a delivery member in its interior. The invention is characterised in that the remover body comprises at least two sets of gripping members extending into its interior and wherein each set of gripping members is configured for gripping a certain type of delivery member shield.

16 Claims, 6 Drawing Sheets

(56) References Cited

U.S. PATENT DOCUMENTS

2010/0016793 A1    1/2010   Jennings et al.
2010/0185148 A1*   7/2010   Gillespie et al. ............. 604/110

FOREIGN PATENT DOCUMENTS

| WO | 2005/115508 | 12/2005 |
|----|-------------|---------|
| WO | 2010/089589 | 8/2010  |

* cited by examiner

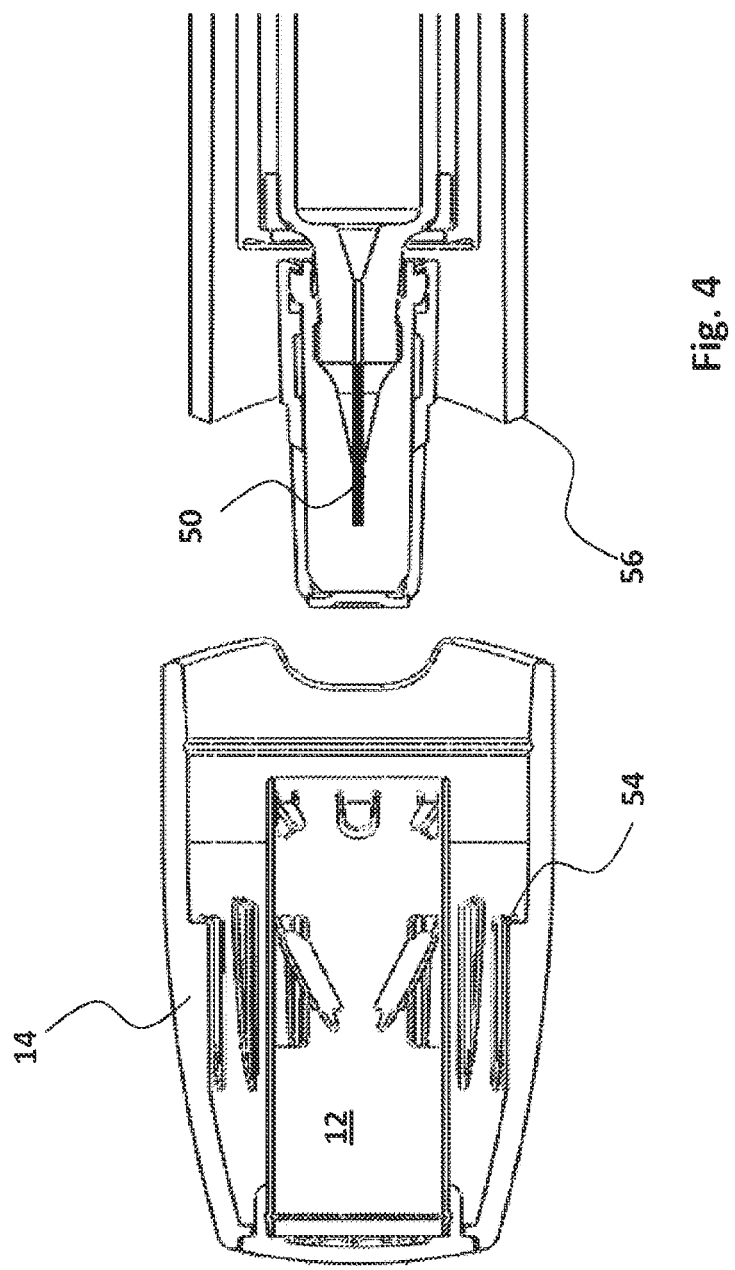

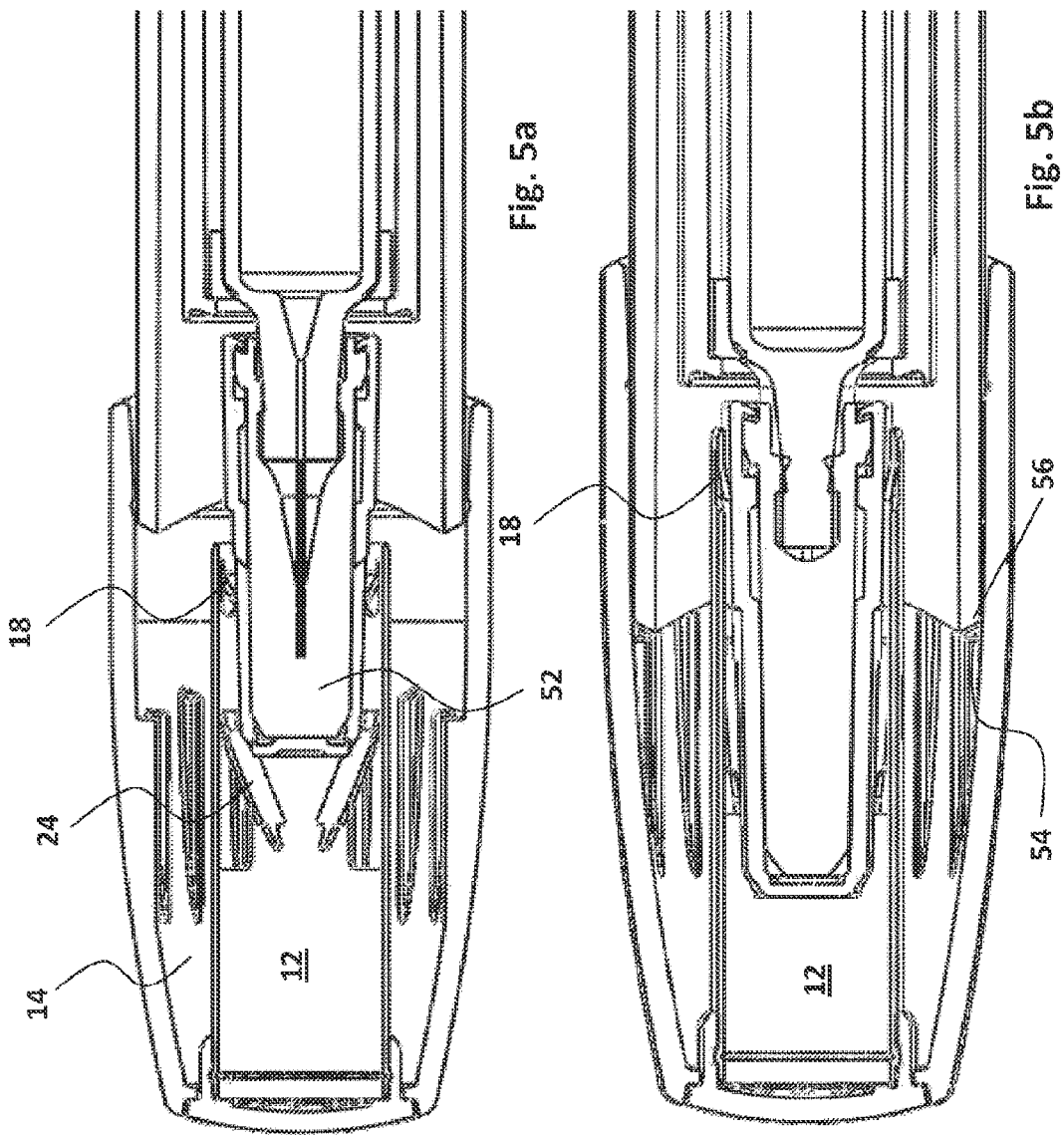

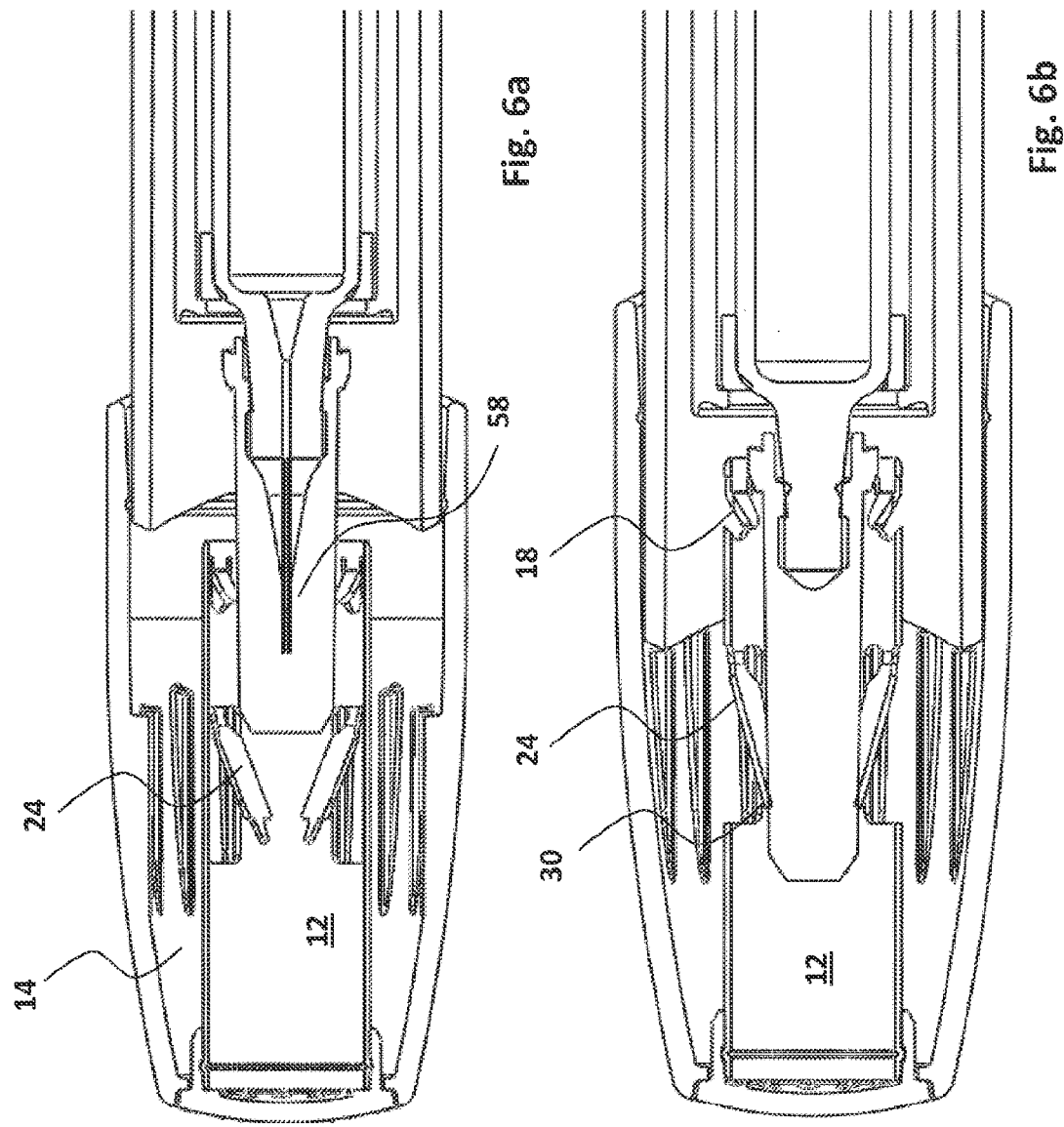

DEVICE FOR REMOVING DELIVERY MEMBER SHIELDS

CROSS REFERENCE TO RELATED APPLICATIONS

The present application is a U.S. National Phase Application pursuant to 35 U.S.C. §371 of International Application No. PCT/SE2012/051051 filed Oct. 2, 2012, which claims priority to Swedish Patent Application No. 1150962-7, filed Oct. 17, 2011 and U.S. Provisional Patent Application No. 61/547,913 filed Oct. 17, 2011. The entire disclosure contents of these applications are herewith incorporated by reference into the present application.

TECHNICAL FIELD

The present invention relates to a device for removing delivery member shields from medicament containers which are intended to be positioned within a medicament delivery device, more specifically a device for removing either rigid or flexible needle shields from cartridges or syringes which are intended to be positioned within an injection device such as a pen injector or an auto-injector.

BACKGROUND

There are a number of medicament delivery devices that have been developed and that are on the market which are intended for self-medication. Many of these devices are provided with medicament containers, to which medicament delivery members such as injection needles are attachable, or integrated with.

Some injectors have been provided with needle shields that are releasably attached to the injection needles. The purpose of the needle shields is to protect the environment against unintentional needle sticks as well as to protect the needle against contamination.

A conventional type of needle shield is a shield or sheath of a resilient and flexible material such as rubber, silicone, or the like. Before the delivery of a drug the flexible needle shield is manually removed by pulling it off the injection needle.

A more recent variant of needle shield is also called rigid needle shield or RNS. An RNS has an inner sheath of resilient and flexible material such as rubber or silicone, which is surrounded by an outer cover of a rigid material such as hard plastic. Before the delivery of a drug the RNS is removed by manually pulling the outer cover off the needle, whereby the inner flexible sheath follows.

In any of the above needle shields, there is a risk that a user is injured on the exposed needle during removal of the needle shield, either if it is a flexible or a rigid needle shield. Some persons may also feel discomfort having to handle components so close to the needles. Because of this, some devices have been developed that can be attached to the needle shields such that the risk of injury is reduced.

One such device is disclosed in WO 2010/089589. There, a medicament delivery device is arranged with an outer forward packaging part at a proximal or front end of the device. When the medicament delivery device is to be used, the forward packaging part is pulled off the device. Inside the forward packaging part a number of fingers are arranged, where each finger is provided with an outwardly extending enlargement and an inwardly extending blade, such that when the forward packaging part is pulled off, the blades grip a rubber needle sheath which surrounds the needle. Thus when the forwards packaging part is removed, so is the rubber sheath.

Document US 2010/0016793 discloses a similar device having a cap with grip means in the form of rearward protrusions which engage a rubber boot surrounding an injection needle when the cap is removed or pulled off a medicament delivery device.

WO 2005/115508 discloses an injection device having a protective cap with which a rigid needle shield may be removed when a dose of medicament is to be delivered. The protective cap is therefore arranged with a castellated washer of metal. When the cap with the washer is pushed onto the rigid needle shield surrounding an injection needle of the medicament delivery device, the washer grips into the rigid plastic material and a firm connection is established. When later the protective cap is removed, the rigid needle shield will follow.

However, even if working properly for the respective type of needle shield, no device has been disclosed that can handle several different types of needle shields, such as e.g. flexible needle shields as well as rigid needle shields. For some medicament delivery devices development has been done for handling different types of medicament containers provided with either rigid needle shields or flexible needle shields. Thus, each type of needle shield requires a certain specific solution that is not easily transferable to the other type of needle shield.

SUMMARY

The aim of the present invention is to remedy the drawbacks of the state of the art devices. More specifically to achieve modularity such that only one device for removing delivery member shields can be used when medicament delivery devices can handle medicament containers provided with different delivery member shields. Therefore, the solution of the present invention comprises means capable of gripping more than one specific type of delivery member shield, more specifically needle shields. Therefore, the device according to the present invention is a device for removing delivery member shields, preferably needle shields, which are intended to cover and protect medicament delivery members which are releasably or fixedly attached to medicament containers intended to be positioned within a medicament delivery device, and wherein said device comprises a remover body arranged to accommodate a delivery member shield in its interior. The device is characterized in that the remover body comprises at least two sets of gripping members extending into its interior and in that each set of gripping members is configured for gripping a certain type of delivery member shield such that a number of different delivery member shields may be handled. The medicament delivery members, preferably injection needles, are releasably or fixedly attached to medicament containers intended to be positioned within a medicament delivery device, preferably an injection device such as a pen injector or an auto-injector.

For example one medicament delivery device could be designed to accommodate medicament containers with different types of delivery member shields, preferably needle shields. In this respect, it could for example be either a flexible needle shield or a rigid needle shield, depending on the type of needle shield that is used for a certain medicament delivery device. In that case the device may be provided with a first set of gripping members capable of gripping a rigid needle shield and a second set of gripping members capable of gripping a flexible needle shield.

A preferable aspect in connection with the remover body is that it may be arranged with at least two sets of gripping members, wherein each set of gripping members is configured and capable of handling a certain type of needle shield, for example either a rigid needle shield or a flexible needle shield.

According to an aspect of the invention, the remover body is an elongated generally tubular body having proximal and distal ends and comprises an inner and outer circumferential surface. Even though a tubular remover body is preferable, other shapes may also be utilized that can provide an enclosure into which a needle shield fit.

According to another aspect of the invention, each set of gripping members is arranged in an annular form on the inner circumferential surface of the remover body and wherein each set of gripping members are formed as a number of elongated members extending into the interior of the remover body at a predetermined angle in relation to a longitudinal axis of the device and towards the proximal end of the remover body.

According to a further aspect of the invention, the elongated members are resilient tongues made integral with the remover body.

According to yet another aspect of the invention, said at least two sets of gripping members are a first set of gripping members arranged or integral to said remover body and capable of gripping a rigid needle shield; and a second set of gripping members arranged or integral to said remover body and capable of gripping a flexible needle shield.

According to a further aspect of the invention, each of the gripping members of the second set comprises an attachment section being somewhat narrower than the rest of the gripping members such that a flexing action in a generally radial direction with reduced force requirements is obtained and wherein the proximal end of each gripping member of the second set is designed or configured with a pointed sharp section and shoulder sections on either side of the pointed section.

According to another aspect of the invention, said first set of gripping members is positioned closest to the distal end of the remover body and said second set of gripping members is positioned closest to the proximal end of the remover body or between the proximal and distal ends of the remover body.

According to a further aspect of the invention, the device further comprises a cap and a lid piece configured to be fixedly connected to each other, preferably the cap comprises a circumferentially extending cut-out configured to interact with radially extending protrusions of a tubular part of the lid piece.

According to yet another aspect of the invention, the lid piece and the remover body are configured to be fixedly connected to each other preferably the lid piece comprises a circumferential groove configured to interact with a circumferential ledge or protrusion of the remover body.

According to another aspect of the invention, said cap is configured to be releasibly attachable to a medicament delivery device and arranged to surround the remover body.

According to a further aspect of the invention, said cap has a general tubular shape having two openings, a proximal opening positioned at the proximal end of the cap and a distal opening positioned at the distal end of the cap and wherein each of said two openings has a plane which is perpendicular to the longitudinal axis of the device.

According to yet another aspect of the invention, said remover body is configured to pass through the proximal opening of the cap after it is fixedly connected to the lid piece such that the tubular part of the lid piece is fitted into said proximal opening.

The elongated members of the gripping members may be arranged flexibly, or yieldingly with regard to a needle shield that enters into the interior of the remover body. This may facilitate the positioning of the needle shield in the interior of the remover body.

According to one aspect of the invention, this flexing or yielding function may be accomplished by the design of the elongated members and by the choice of material. Regarding the design of the elongated members, they may be in the form of tongues having a certain width giving them certain stability, and a thickness, which is less than the width for providing a flexing or bending function. Regarding the choice of material, it may comprise a metal material or a plastic material capable of displaying an elastic function for certain force levels. Thereby, the elongated members may be moved somewhat when a needle shield is introduced in the remover body.

Further, the elongated members of the gripping members may extend into the interior of the remover body at a certain angle in relation to the longitudinal axis of the device and preferably in a proximal direction. With this design it is possible to enter a needle shield into the interior of the remover body whereby the elongated members yield and slide along the surface of the needle shield in one direction.

Regarding rigid needle shields having surface materials that are rather hard, it may be an advantage to provide a grip of the needle shield at a distal area of the outer surface of the rigid needle shield. Therefore, the first set of gripping members may preferably be arranged in a distal area of the remover body so that the gripping members will pass the entire needle shield during insertion of the needle shield into the remover body. The length and position of the first set of gripping members may in this aspect be such that they are forced somewhat in the generally radial direction when a rigid needle shield is inserted. This design of radial flexing action may provide a firm gripping action at the distal area of the rigid needle shield.

During insertion into the remover body, the second set of gripping members may also be forced somewhat in the generally radial direction by the rigid needle shield but in order not to exert unnecessary forces on the outer surface of the rigid needle shield, the elongated members of the second set of gripping members may be designed with reduced flexing force such that the force from the second gripping members is rather low during insertion of the rigid needle shield. The force reduction may be done by removing material at a certain section of the elongated members, such as for instance in the area where they are connected or attached to the remover body.

Regarding a flexible needle shield, the second set of gripping members may as stated above have a reduced flexing force such that insertion of a flexible needle shield into the remover body is facilitated. Proximal ends of the elongated members of the second set of gripping members then slide along the outer surface of the flexible needle shield. This is an advantage when later the flexible needle shield is to be removed. Since the proximal ends of the elongated members are in contact with the surface of the needle shield and since the elongated members may have a certain inclination in relation to the longitudinal axis of the device, the proximal ends of the elongated members are forced against the surface of the flexible needle shield and into the material as the remover body is pulled off the delivery device since the shield is flexible and resilient.

In order to enhance the gripping effect of the elongated members of the second set of gripping members, the proximal ends may preferably be arranged with grip enhancing features. These features may increase the friction between the elongated members in order to ascertain a proper gripping contact. According to one aspect of the invention, the grip enhancing feature may comprise a pointed end section capable of entering into the material of the flexible needle shield. However, in order to limit the penetration depth, a stop surface or shoulder section may be provided adjacent the pointed section. In this manner the elongated members will provide a firm grip and at the same time the risk of damaging the flexible needle shield is reduced.

According to a further aspect of the invention, the remover body may be connectable to a cap or the like housing part of the medicament delivery device that may surround at least the needle shield and the injection needle therein, and which cap may be removable when a dose of medicament is to be delivered.

In this aspect, the cap may be provided with an opening or passage in the proximal direction. This passage may preferably be designed to accommodate the insertion of the remover body, so that the remover body in turn may accommodate the needle shield.

The remover body may in this aspect be arranged with a lid member attached to its proximal end, such that the passage of the cap may be closed when the remover body has been inserted into the cap. In order to properly accommodate the lid member, the passage of the cap may be arranged with a circumferential cut-out, into which the periphery of the lid member may be positioned. Further, in order to ascertain a good seating of the lid member, and a good connection between the lid member/remover body and the protective cap, the lid member may be arranged with locking members that engage the passage of the protective cap.

The solution according to the present invention can thus provide the possibility of handling rigid needle shields as well as flexible needle shields with one unit due to the design of the remover body with at least two sets of gripping members. Also other types of needle shields may be handled by providing appropriate gripping members.

This solution may facilitate the handling of different medicament containers and different needle shields with the same medicament delivery device, thereby reducing the need for special solutions otherwise required. The first and the second set of gripping members according to the present invention do not interfere or disturb the handling of any types of needle shields.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIG. 4 is a cross-sectional view of the device according to the present invention before attachment to a proximal end of a medicament delivery device, FIGS. 5*a, b* are cross-sectional views how the device according to the present invention functions with a rigid needle shield where FIG. 5*a* shows an intermediate position and FIG. 5*b* shows an end position, and FIGS. 6*a, b* are cross-sectional views how the device according to the present invention functions with a flexible needle shield where FIG. 6*a* shows an intermediate position and FIG. 6*b* shows an end position.

DETAILED DESCRIPTION

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the medicament delivery device is located closest to the medicament delivery site of the patient.

Figure 1:
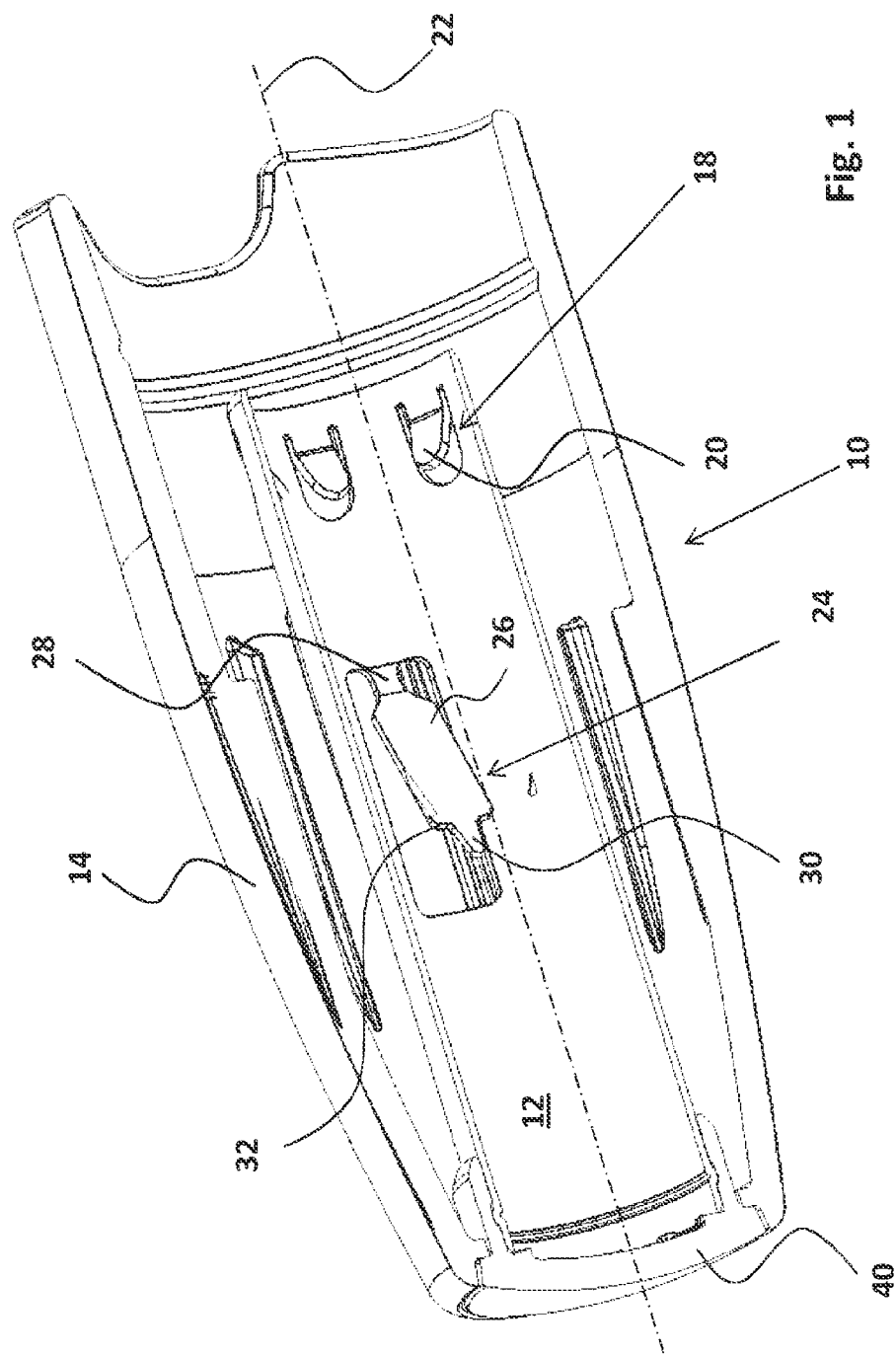
FIG. 1 is a cross-sectional perspective view of a device according to one embodiment of the invention.

The delivery member shield removing device, preferably a needle shield removing device 10 comprises, in the shown embodiment, a remover body 12 extending along a longitudinal axis 22 of the device, FIG. 1, and configured to receive a delivery member shield in its interior, preferably a needle shield. The device may also include a cap 14 removably arranged to the proximal end of a medicament delivery device, preferably an injection device, and/or more preferably an auto-injector. The device further comprises a lid piece 40, wherein the cap 14 and the lid piece 40 are configured to be fixedly connected to each other, and wherein the lid piece 40 and the remover body 12 are configured to be fixedly connected to each other.

The Cap

Figure 2:
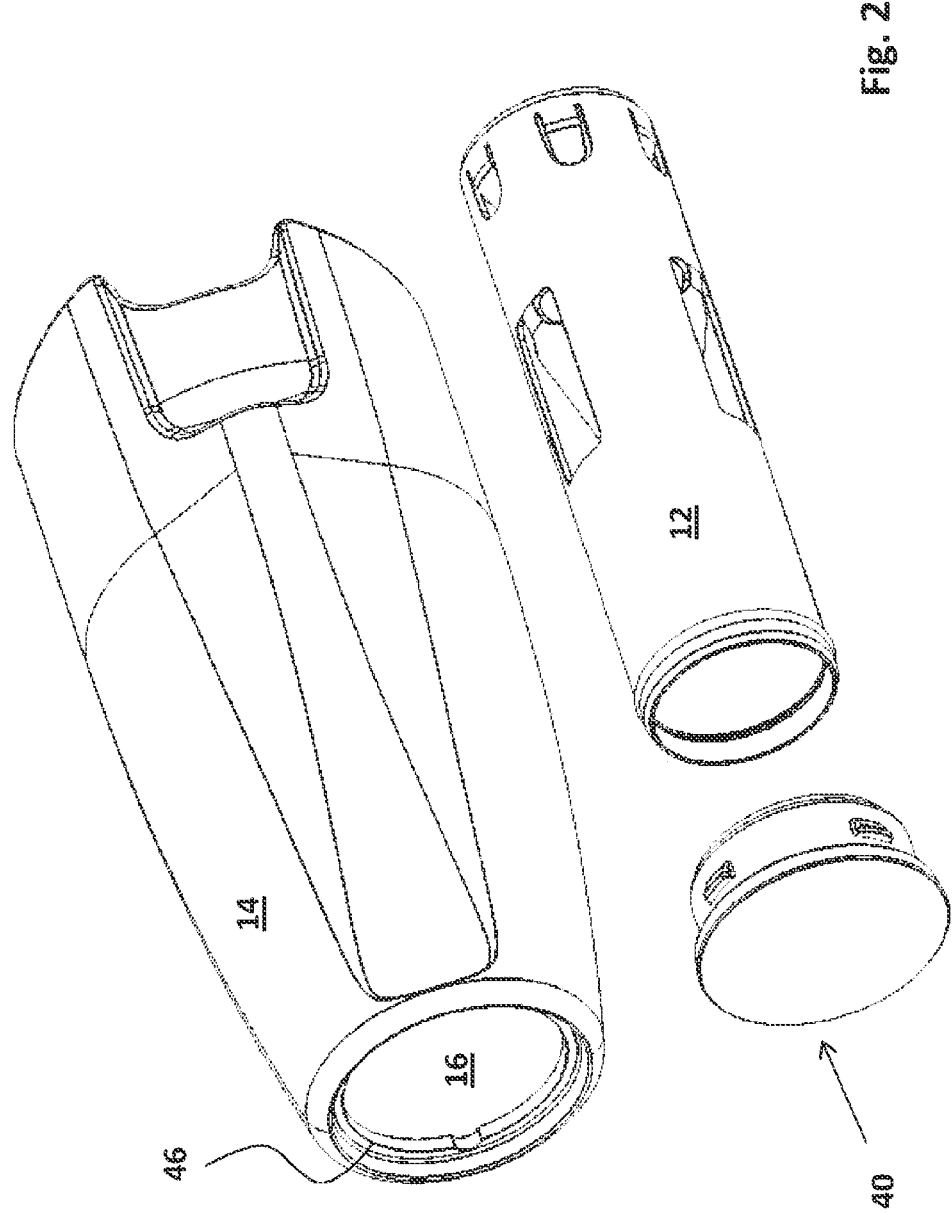
FIG. 2 is an exploded view of the device according to FIG. 1.

The cap has preferably a general tubular shape having two openings, a proximal opening 16 positioned at the proximal end of the cap and a distal opening positioned at the distal end of the cap, FIG. 2, and wherein each of said two openings is parallel to a plane which is perpendicular to the longitudinal axis 22 of the device. Further, the proximal opening 16 preferably has a circumferentially extending cut-out 46, FIG. 2.

The Lid Piece

Figure 3:
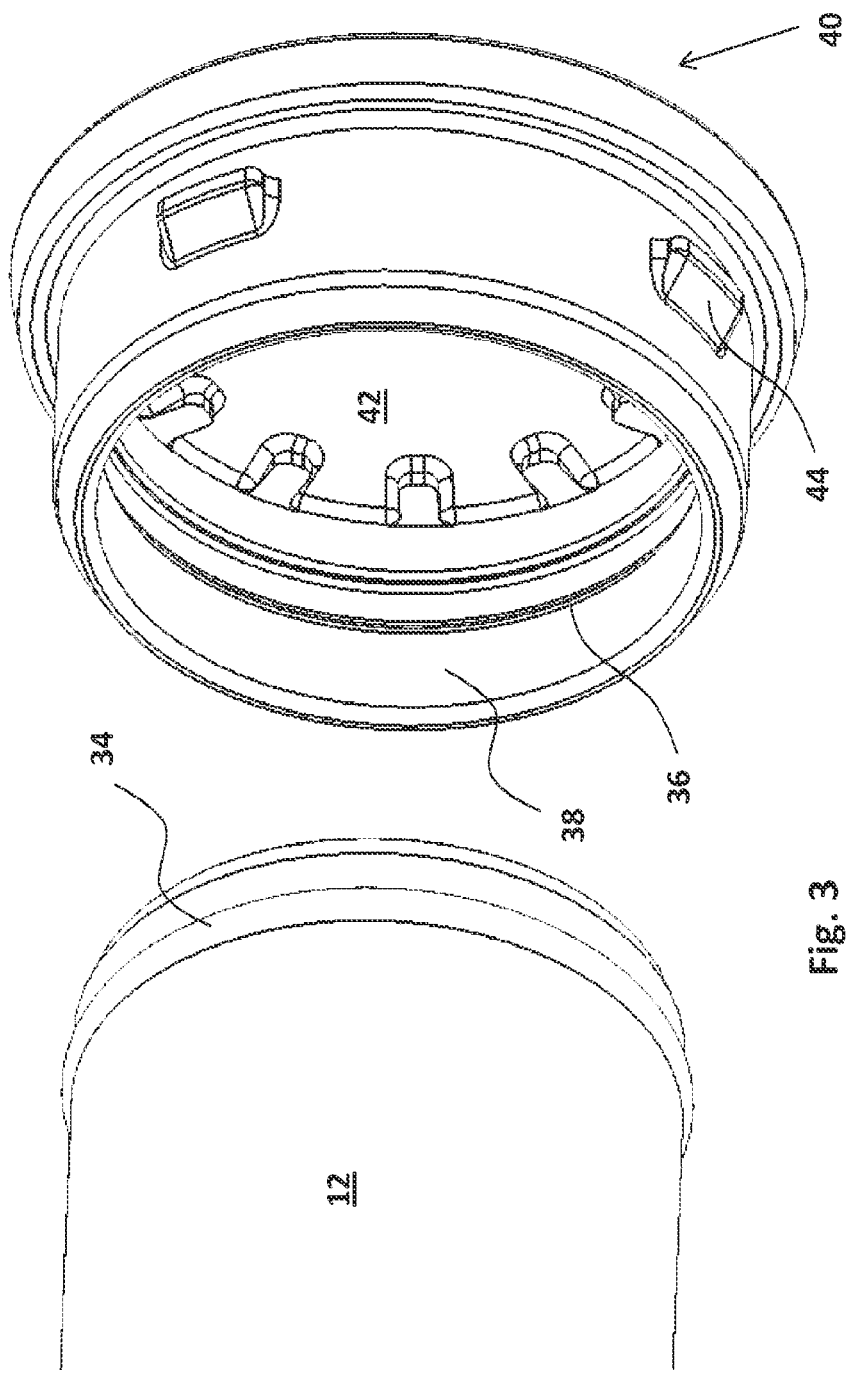
FIG. 3 is a detailed perspective view of a lid member comprised in the present invention.

The lid piece 40, FIG. 3, comprises a generally tubular part 38 and an end surface 42 arranged to, or integral with, the proximal end of the tubular part. The end surface 42 has preferably a circular configuration and is perpendicular in relation to the longitudinal axis 22 of the device. Further, the end surface extends radially somewhat outside the tubular part 38. The tubular part 38 comprises an inner and an outer circumferential surface. Preferably a number of radially extending protrusions 44 are arranged to, or integral with, the outer surface of the tubular part. More preferably, the protrusions 44 are arranged at a predetermined distance from each other. Further, a circumferential groove 36 is arranged on the inner circumferential surface of the tubular part 38.

The Remover Body

The remover body 12 is an elongated generally tubular body comprising an inner and outer circumferential surface. The remover body further comprises at least two sets of gripping members extending into its interior and wherein each set of gripping members is configured for gripping a certain type of delivery member shield. Preferably, each of said first and second set of gripping members is arranged in an annular form on the inner circumferential surface of the remover body. More particularly, each set of gripping members is formed as a number of elongated members extending into the interior of the remover body at a predetermined angle in relation to a longitudinal axis 22 of the device and towards the proximal end of the remover body 12. Preferably, the elongated members are resilient tongues made integral with the remover body 12. In this context it is feasible that the remover body is made of a material that permits a forming action such as bending, melting or other plastic deformation, such that the members 18 receive a direction as described above. Further the material of the members is chosen such that the members receive a certain flexibility or resiliency in a generally radial direction of the remover body. Further, the remover body 12 is preferably provided with a circumferentially extending ledge or protrusion 34, FIG. 3, on its outer circumferential surface and positioned at a predetermined distance from its proximal end.

Preferably the remover body comprises a first 18 and a second 24 set of gripping members, FIG. 1, arranged on the inner circumferential surface of the remover body, more preferably each of said first and second set of gripping members being arranged in an annular form on the inner circumferential surface of the remover body.

Preferably, the first set of gripping members 18 is positioned closest to the distal end of the remover body, more preferably at a predetermined distance from the distal end of the remover body. Gripping members 20 of the first set are in the embodiment shown formed as a number of elongated members extending into the interior of the remover body at an angle in relation to the longitudinal axis 22 of the device and towards the proximal end of the remover body 12. Preferably the elongated members may be tongues made integral with the remover body 12. The function of the first set of gripping members 18 will be described in detail below.

The second set of gripping members 24, FIG. 1, is preferably positioned closest to the proximal end of the remover body or between the proximal and distal ends of the remover body. As illustrated in FIG. 1, the second set of gripping members 18 extends further into the remover body 12 than the first set 18. More preferably at a more proximal position in relation to the first set of gripping members 18. Gripping members 26 of the second set are in the embodiment shown formed as a number of elongated members extending into the interior of the remover body 12 at an angle in relation to the longitudinal axis 22 of the device and towards the proximal end of the remover body 12. Preferably the elongated second gripping members 26 may be tongues made integral with the remover body 12. Preferably each of the gripping members of the second comprises an attachment section 28 being somewhat narrower than the rest of the gripping member in order to obtain a flexing action in a generally radial direction with reduced force requirements. Further, the proximal end of each gripping member of the second set is designed or configured with a pointed sharp section 30 and shoulder sections 32 on either side of the pointed sharp section 30. The function of the second set of gripping members 24 will be described in detail below.

The ledge or protrusion 34 of the remover body 12 is intended to cooperate with the circumferential groove 36 of the lid piece 40, FIG. 3, for attaching or fixedly connecting the remover body 12 to the lid piece 40. After the remover body and the lid piece are attached or fixedly connected to each other, the remover body 12 which is configured to pass through the proximal opening 16 of the cap 14, is inserted through the proximal opening 16 of the cap 14 whereby the protrusions 44 of the tubular part 38 of the lid piece 40 co-act with the circumferentially extending cut-out 46 of the cap 14, such that the lid piece 40 is locked or fixedly connected to the cap 14, thereby forming the delivery member shield removing device, more preferably the needle shield removing device 10.

When assembling the delivery member shield removing device to the medicament delivery device, the delivery member shield removing device is axially moved towards the proximal end of the medicament delivery device, FIG. 4, such that the delivery member shield enters the interior of the remover body 12 and wherein at least one of the at least two sets of gripping members interacts with or abuts the delivery member shield.

Rigid Needle Shield

If the medicament delivery device is arranged with an injection needle 50 that is covered by a rigid needle shield 52, FIG. 5, when the rigid needle shield 52 enters the interior of the remover body 12, the first set of gripping members 18 will come in contact or interact with the outer surface of the rigid needle shield and will be pushed somewhat outwards in the radial direction, FIG. 5a, and thereafter slide along the outer surface of the rigid needle shield until a distally directed abutment surface 54 of the cap 14 comes in contact with a proximally directed end surface 56 of the housing of the medicament delivery device, FIG. 5b. In this position, the first set of gripping members 18 are positioned at a distal area of the rigid needle shield with the proximal ends of the first set of gripping members 18 pushing against the surface of the rigid needle shield due to the flexing force in the generally radial direction of the first set of gripping members, FIG. 5b.

During the insertion of the rigid needle shield 52 into the remover body 12, the second gripping members 24 will be pushed in the generally radial direction when in contact with the rigid needle shield, FIG. 5b, and the pointed sharp section 30 will slide against the outer surface of the rigid needle shield, but the force from the second set of gripping members 24 will be rather small due to the reduced material area 28, which reduces the flexing force of the second set of gripping members 24 against the outer surface of the rigid needle shield.

When the cap 14 with the remover body 12 has reached its end position, FIG. 5b, the cap 14 and thus the rigid needle shield 52 is ready to be removed for a delivery of a dose of medicament. When the cap 14 is removed by pulling it towards the proximal direction in relation to the medicament delivery device, the remover body 12 will also follow. The movement in the proximal direction of the remover body 12 causes the proximally directed first set of gripping members 18 to grip firmly into the surface of the rigid needle shield. Thereby the rigid needle shield 52 is removed when the protective cap 14 and the remover body 12 are removed. The injection needle is now free to be used for penetration and injection of a dose of medicament.

Flexible Needle Shield

If the medicament delivery device is arranged with an injection needle 50 that is covered by a flexible needle shield 58, FIG. 6a, when the flexible needle shield enters the interior of the remover body 12, the first set of gripping members 18 will move outside the outer surface of the flexible needle shield until the cap 14 is in position in relation to the housing of the medicament delivery device as described above. During this movement, the set of second gripping members 24 will be pushed in the generally radial direction when in contact with the flexible needle shield and will slide against the outer surface of the needle shield, FIG. 6a.

When the cap 14 has reached its end position, FIG. 6b, the cap 14 and thus the flexible needle shield 58 is ready to be removed for a delivery of a dose of medicament. When the cap 14 is removed by pulling it in the proximal direction in relation to the medicament delivery device, the remover body 12 will also follow. The movement in the proximal direction of the remover body 12 causes the pointed sections 30 of the second set of gripping members 24 to be pushed into the material of the flexible needle shield due to the inclined position of the second set of gripping members 24. However, the movement of the second set of gripping members 24 in relation to the flexible needle shield is stopped when the shoulder sections 32 abut the surface of the needle shield. Further movement of the remover body 12 and its set of second gripping members 24 will now cause the flexible needle shield to move along as a unit. Thereby the flexible needle shield is removed when the cap 14 with the remover body 12 are removed. The injection needle is now free to be used for penetration and injection of a dose of medicament.

It is to be understood that the embodiment described above and shown in the drawings is to be regarded only as a non-limiting example of the invention and that it may be modified in many ways within the scope of the patent claims.

The invention claimed is:

1. A device for removing delivery member shields which are intended to cover and protect medicament delivery members which are releasably or fixedly attached to medicament containers intended to be positioned within a medicament delivery device, the device comprises:
   a cap;
   a lid piece comprising inner and outer circumferential surfaces;
   a remover body directly attached to the lid piece through engagement with the inner circumferential surface, where the remover body is configured to accommodate a delivery member shield in an interior of the remover body, where the remover body comprises at least two sets of gripping members extending into the interior,
   wherein each set of gripping members is configured for gripping a certain type of delivery member shield such that one set of gripping members extends into the interior of the remover body less distance than a distance of extension of the other set of gripping members.

2. The device according to claim 1, wherein the remover body is an elongated generally tubular body having proximal and distal ends and comprising an inner and outer circumferential surface.

3. The device according to claim 2, wherein each set of gripping members is arranged in an annular form on the inner circumferential surface of the remover body and wherein each set of gripping members are formed as a number of elongated members extending into the interior of the remover body at a predetermined angle in relation to a longitudinal axis of the device and towards the proximal end of the remover body.

4. The device according to claim 3, wherein the elongated members are resilient tongues made integral with the remover body.

5. The device according to claim 1, wherein a first set of gripping members is configured to grip a rigid needle shield and a second set of gripping members is configured to grip a flexible needle shield.

6. The device according to claim 5, wherein each of the gripping members of the second set comprises an attachment section being narrower than the rest of the gripping members such that a flexing action in a generally radial direction with reduced force requirements is obtained and wherein the proximal end of each gripping member of the second set is designed or configured with a pointed sharp section and shoulder sections on either side of the pointed sharp section.

7. The device according to claim 5, wherein the first set of gripping members is positioned closest to a distal end of the remover body and wherein the second set of gripping members is positioned closest to a proximal end of the remover body or between the proximal and distal ends of the remover body.

8. The device according to claim 1, wherein the cap and the lid piece are fixedly connected to each other through a circumferentially extending cut-out configured to interact with radially extending protrusions of a tubular part of the lid piece.

9. The device according to claim 8, wherein the lid piece and the remover body are configured to be fixedly connected to each other, preferably the lid piece comprises a circumferential groove configured to interact with a circumferential ledge or protrusion of the remover body.

10. The device according to claim 8, wherein the cap is configured to be releasably attachable to a medicament delivery device and arranged to surround the remover body.

11. The device according to claim 8, wherein the cap has a general tubular shape having two openings, a proximal opening positioned at a proximal end of the cap and a distal opening positioned at a distal end of the cap and wherein each of the two openings is parallel to a plane which is perpendicular to the longitudinal axis of the device.

12. The device according to claim 11, wherein the remover body is configured to pass through the proximal opening of the cap after the remover body is fixedly connected to the lid piece such that the tubular part of the lid piece is fitted into the proximal opening.

13. A medicament delivery device comprising the device according to claim 1.

14. The medicament delivery device according to claim 13 wherein the medicament delivery device is an injection device.

15. The medicament delivery device according to claim 14 wherein the injection device is a pen injector or an auto-injector.

16. A device for removing delivery member shields which are intended to cover and protect medicament delivery members which are releasably or fixedly attached to medicament containers intended to be positioned within a medicament delivery device, the device comprises a remover body configured to accommodate a delivery member shield in an interior of the remover body, where the remover body comprises at least two sets of gripping members extending into the interior,
   wherein each set of gripping members is configured for gripping a certain type of delivery member shield such that one set of gripping members extends into the interior of the remover body less distance than a distance of extension of the other set of gripping members,
   wherein each of the gripping members of the second set comprises an attachment section being narrower than the rest of the gripping members such that a flexing action in a generally radial direction with reduced force requirements is obtained and wherein a proximal end of each gripping member of the second set is designed or configured with a pointed sharp section and shoulder sections on either side of the pointed sharp section.

* * * * *